(12) United States Patent
Cutrupi

(10) Patent No.: US 9,144,554 B2
(45) Date of Patent: Sep. 29, 2015

(54) TOPICAL COMPOSITIONS FOR USE IN THE PREVENTION AND/OR TREATMENT OF DERMATITIS

(71) Applicant: Carmelo Cutrupi, Bolzano (IT)

(72) Inventor: Carmelo Cutrupi, Bolzano (IT)

( * ) Notice: Subject to any disclaimer, the term of this patent is extended or adjusted under 35 U.S.C. 154(b) by 0 days.

(21) Appl. No.: 14/588,480

(22) Filed: Jan. 2, 2015

(65) Prior Publication Data
US 2015/0126476 A1    May 7, 2015

Related U.S. Application Data

(63) Continuation of application No. 14/130,513, filed as application No. PCT/EP2012/058974 on May 15, 2012, now abandoned.

(30) Foreign Application Priority Data

Jul. 6, 2011    (IT) .............................. MI2011A1260

(51) Int. Cl.
| | |
|---|---|
| *A61K 31/025* | (2006.01) |
| *A61K 9/00* | (2006.01) |
| *A61K 31/695* | (2006.01) |
| *A61K 31/185* | (2006.01) |
| *A61K 31/035* | (2006.01) |
| *A61K 31/192* | (2006.01) |

(52) U.S. Cl.
CPC ............. *A61K 31/025* (2013.01); *A61K 9/0014* (2013.01); *A61K 31/035* (2013.01); *A61K 31/185* (2013.01); *A61K 31/192* (2013.01); *A61K 31/695* (2013.01)

(58) Field of Classification Search
CPC . A61K 31/695; A61K 31/035; A61K 31/185; A61K 31/025; A61K 31/19; A61K 31/0252
USPC ...................................... 514/63, 576; 570/187
See application file for complete search history.

(56) References Cited

U.S. PATENT DOCUMENTS

| | | | |
|---|---|---|---|
| 2003/0170280 A1 * | 9/2003 | Canham et al. | ............... 424/401 |
| 2007/0020304 A1 | 1/2007 | Tamarkin et al. | |
| 2008/0292560 A1 * | 11/2008 | Tamarkin et al. | ............... 424/45 |

FOREIGN PATENT DOCUMENTS

| | | | |
|---|---|---|---|
| WO | 98/11882 | | 3/1998 |
| WO | WO 98/11882 | * | 3/1998 |

OTHER PUBLICATIONS

International Search Report issued in counterpart PCT Application No. PCT/EP2012/058974.
Written Opinion of International Searching Authority issued in counterpart PCT Application No. PCT/EP2012/058974.

* cited by examiner

*Primary Examiner* — Blessing M Fubara
(74) *Attorney, Agent, or Firm* — Silvia Salvadori P.C.

(57) ABSTRACT

The present invention relates to the use of topical compositions containing bromociclen for the prevention and/or treatment of various types of dermatitis, in particular eczema and psoriasis.

15 Claims, No Drawings

TOPICAL COMPOSITIONS FOR USE IN THE PREVENTION AND/OR TREATMENT OF DERMATITIS

This U.S. non-provisional application is a continuation of U.S. application Ser. No. 14/130,513 filed on Feb. 21, 2014, which is a U.S. National Stage of PCT/EP2012/058974 filed on May 15, 2012, which claims priority to and the benefit of Italian Application No. MI2011A001260 filed on Jul. 6, 2011, the contents of which are incorporated herein by reference in their entireties.

FIELD OF INVENTION

The present invention relates to the use of topical compositions containing bromociclen for the prevention and/or treatment of dermatitis.

STATE OF THE ART

Dermatitis is a skin disease consisting of an inflammatory reaction of the skin manifested as an irritation. Dermatitis can have very different causes, which may, for example, be chemical, physical, microbial or parasitic.

Dermatitis can also be the result of a skin disease with allergic causes, such as atopic eczema or neurodermitis, or autoimmune causes, such as psoriasis.

Non-contagious forms of dermatitis are also called eczema.

Dermatitis often flares up in situations of stress.

Eczema is by definition an inflammatory reaction of the dermis (dermatitis), which is itchy and non-contagious.

The most common forms of eczema are neurodermitis (also called atopic eczema or atopic dermatitis), typical of the face, which is a chronic or chronic/relapsing disorder, triggered by various factors which may be immunological or non-immunological; allergic dermatitis, also known as contact dermatitis; steatotic eczema; dyshidrotic eczema, which appears on the fingers, the palms of the hands and the soles of the feet; discoid eczema, which mainly appears on the limbs; and seborrhoeic dermatitis.

The treatment of eczema depends on the form in which it is manifested; however, cortisone treatments, topical steroids, emollients and moisturisers are generally used.

Psoriasis, which is one of the most common chronic forms of skin disease in the world, occurs in 1.4-4.82% of the world's population.

It is an inflammatory, non-infectious skin disease which is usually chronic and relapsing.

The most common manifestations are well-defined erythematous papules and plaques covered with silvery or pearly scales. The lesions are of various sizes, and their severity can range from a few points of dandruff-like flaking to general dermatosis with arthritis (psoriatic arthritis), exfoliations and debilitating eruptions.

The lesions most often occur in the scalp, the extensor areas of the elbow and knee and the lumbosacral area, but in some forms also appear in the flexor areas, on the genitals, the soles of the feet and the palms of the hands.

Various forms of psoriasis exist, such as discoid (the most common form), plaque, guttate and inverse psoriasis.

Psoriasis treatments include, as first-choice medicaments in forms of limited extent, topical emollients such as vaseline; cortisone and/or reducing agents; keratolytic agents and vitamin D analogues.

The disorders described above are highly debilitating, from the psychological as well as the physical standpoint.

The medicaments used to treat dermatitis include methotrexate and ivermectin, which have proved toxic.

The treatments currently available do not produce a complete, permanent cure of the disease, and/or their use triggers a variety of side effects.

As these disorders are so widespread, there is still a need to use alternative preparations for the prevention and/or treatment of dermatitis, especially eczema and psoriasis.

SUMMARY OF THE INVENTION

The present invention relates to topical compositions containing bromociclen for use in the prevention and/or treatment of dermatitis.

DESCRIPTION OF THE INVENTION

It has surprisingly been found that compositions containing bromociclen are useful in the prevention and/or treatment of dermatitis.

Bromociclen, 5-(bromomethyl)-1,2,3,4,7,7-hexachlorobicyclo[2.2.1]-hept-2-ene, is a compound of formula:

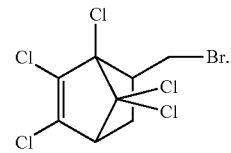

The compositions according to the invention have proved effective in the treatment of keratosis and/or inflammatory disorders of the skin and dermis. The topical compositions are useful in particular in the prevention and/or treatment of eczema (such as atopic dermatitis) and psoriasis (such as plaque psoriasis).

The compositions according to the invention can also include, as active constituents, silicic acid and/or methyltaurine oleate sodium salt and/or 6-chloro-3-hydroxy-1-methylbenzol.

Said compositions are administered topically.

The present invention relates to pharmaceutical compositions containing bromociclen, and optionally silicic acid and/or methyltaurine oleate sodium salt and/or 6-chloro-3-hydroxy-1-methylbenzol, and at least one pharmaceutically acceptable excipient or carrier.

The pharmaceutically acceptable excipients or carriers can be, for example, water, ethyl alcohol, surfactants and other suitable excipients or carriers according to the International Pharmacopoeia.

The topical compositions can be formulated by conventional methods.

The preferred dosage forms are, for example, solutions, lotions, gels, creams, ointments, shampoos, impregnated bandages and other suitable dosage forms according to the International Pharmacopoeia.

According to a preferred aspect, the compositions are employed for human use.

The examples given below further illustrate the invention.

EXAMPLE

An experimental study was conducted to test the efficacy of the topical compositions in the treatment of dermatitis.

The trial was conducted using solutions with different concentrations of the active constituents according to the severity of the disease treated.

26 volunteers took part in the trial.

The patients were treated for a period ranging from 1 week to 4 months with the solution according to the invention applied topically twice a day (morning and evening), according to individual tolerance and the disease treated.

Efficacy Evaluation

The extent and severity of the dermatitis in each patient was determined before and after treatment on the basis of the following scale from 0 to 10:

0=Total absence of the symptoms and the disease
1=Almost total absence of the symptoms and the disease
2=Cure of the majority of the symptoms and the disease
3=Good improvement in the symptoms and the disease
4=Improvement in the symptoms and the disease
5=Slight improvement in the symptoms and the disease
6=Gradual improvement in some symptoms
7=Slight improvement in some symptoms
8=Persistence of 50% of the lesions
9=Persistence of some symptoms and the lesions
10=Unchanged persistence of the symptoms and the disease.

The evaluation before and after the treatment was conducted by the physician investigator.

The results are set out in the Table.

TABLE

| Patient | Evaluation before treatment | Evaluation after treatment | Disorder |
| --- | --- | --- | --- |
| 1 | 10 | 0 | Psoriasis vulgaris |
| 2 | 9 | 0 | Psoriasis vulgaris |
| 3 | 9 | 1 | Psoriasis vulgaris |
| 4 | 10 | 1 | Psoriasis vulgaris |
| 5 | 10 | 1 | Psoriasis vulgaris |
| 6 | 10 | 2 | Psoriasis vulgaris |
| 7 | 10 | 2 | Psoriasis vulgaris |
| 8 | 9 | 2 | Psoriasis vulgaris |
| 9 | 9 | 0 | Psoriasis vulgaris |
| 10 | 9 | 0 | Psoriasis vulgaris |
| 11 | 10 | 1 | Intertriginous psoriasis |
| 12 | 9 | 0 | Pustular psoriasis |
| 13 | 9 | 0 | Discoid psoriasis |
| 14 | 10 | 1 | Atopic dermatitis |
| 15 | 9 | 1 | Atopic dermatitis |
| 16 | 9 | 0 | Atopic dermatitis |
| 17 | 10 | 1 | Atopic dermatitis |
| 18 | 10 | 1 | Atopic dermatitis |
| 19 | 10 | 0 | Atopic dermatitis |
| 20 | 10 | 1 | Atopic contact dermatitis |
| 21 | 9 | 1 | Atopic contact dermatitis |
| 22 | 10 | 1 | Atopic contact dermatitis |
| 23 | 10 | 0 | Atopic contact dermatitis |
| 24 | 9 | 0 | Exfoliative eczematous dermatitis |
| 25 | 10 | 0 | Dyshidrotic eczema |
| 26 | 9 | 1 | Discoid eczema |

Conclusions

The opinions of the efficacy of the composition expressed by the physician investigator after the treatment indicated that the composition according to the invention is effective in the treatment of psoriasis vulgaris, intertriginous psoriasis, pustular psoriasis, discoid psoriasis, atopic dermatitis, atopic contact dermatitis, exfoliative eczematous dermatitis, dyshidrotic eczema and discoid eczema.

These results were confirmed by the opinions of the volunteers, who considered that the composition was effective.

The invention claimed is:

1. Methods of treating dermatitis in patients in need thereof, said methods comprising topically administering to said patients an effective amount of topical compositions comprising bromociclen in water; and
treating said patients.

2. Methods as claimed in claim 1, wherein said topical compositions further comprise silicic acid.

3. Methods as claimed in claim 1, wherein said topical compositions further comprise methyltaurine oleate sodium salt.

4. Methods as claimed in claim 1, wherein said topical compositions further comprise silicic acid, methyltaurine oleate sodium salt and 6-chloro-3-hydroxy-1-methylbenzol.

5. Methods as claimed in claim 1, wherein said topical compositions further comprise 6-chloro-3-hydroxy-1-methylbenzol.

6. Methods of treating eczema in patients in need thereof, said methods comprising topically administering to said patients an effective amount of topical compositions comprising bromociclen in water; and
treating said patients.

7. Methods as claimed in claim 6, wherein said topical compositions further comprise silicic acid.

8. Methods as claimed in claim 6, wherein said topical compositions further comprise methyltaurine oleate sodium salt.

9. Methods as claimed in claim 6, wherein said topical compositions further comprise silicic acid, methyltaurine oleate sodium salt and 6-chloro-3-hydroxy-1-methylbenzol.

10. Methods as claimed in claim 6, wherein said topical compositions further comprise 6-chloro-3-hydroxy-1-methylbenzol.

11. Methods of treating psoriasis in patients in need thereof, said methods comprising topically administering to said patients an effective amount of topical compositions comprising bromociclen in water; and
treating said patients.

12. Methods as claimed in claim 11, wherein said topical compositions further comprise silicic acid.

13. Methods as claimed in claim 11, wherein said topical compositions further comprise methyltaurine oleate sodium salt.

14. Methods as claimed in claim 11, wherein said topical compositions further comprise silicic acid, methyltaurine oleate sodium salt and 6-chloro-3-hydroxy-1-methylbenzol.

15. Methods as claimed in claim 11, wherein said topical compositions further comprise 6-chloro-3-hydroxy-1-methylbenzol.

* * * * *